US011691943B2

(12) United States Patent
Huang et al.

(10) Patent No.: US 11,691,943 B2
(45) Date of Patent: Jul. 4, 2023

(54) PREPARATION METHOD OF 4-(HEPTAFLUORO-2-PROPYL)-2-TRIFLUOROMETHYLANILINE AND APPLICATION THEREOF

(71) Applicant: JIANGXI TIANYU CHEMICAL CO., LTD., Ji'an (CN)

(72) Inventors: Chaoqun Huang, Ji'an (CN); Jintao Zhu, Ji'an (CN); Liangming Luo, Ji'an (CN); Rong Zhang, Ji'an (CN)

(73) Assignee: JIANGXI TIANYU CHEMICAL CO., LTD.

( * ) Notice: Subject to any disclaimer, the term of this patent is extended or adjusted under 35 U.S.C. 154(b) by 0 days.

(21) Appl. No.: 17/686,997

(22) Filed: Mar. 4, 2022

(65) Prior Publication Data
US 2023/0062431 A1    Mar. 2, 2023

(30) Foreign Application Priority Data
Mar. 10, 2021 (CN) .......................... 202110260878.9

(51) Int. Cl.
C07C 209/74 (2006.01)
B01J 31/02 (2006.01)
C07C 209/86 (2006.01)
C07C 211/52 (2006.01)

(52) U.S. Cl.
CPC ......... *C07C 209/74* (2013.01); *B01J 31/0239* (2013.01); *C07C 209/86* (2013.01); *C07C 211/52* (2013.01)

(58) Field of Classification Search
CPC ... C07C 209/68; C07C 209/00; C07C 211/43; C07C 211/44; C07C 211/45; C07C 211/46; C07C 211/47; A01N 37/22
See application file for complete search history.

(56) References Cited

U.S. PATENT DOCUMENTS

| | | | | |
|---|---|---|---|---|
| 9,890,110 | B2 * | 2/2018 | Aoki | C07C 233/81 |
| 10,822,816 | B2 * | 11/2020 | Coughlan | E04F 21/248 |
| 2011/0136878 | A1 * | 6/2011 | Kobayashi | C07C 311/32 |
| | | | | 546/310 |
| 2011/0201687 | A1 * | 8/2011 | Kobayashi | C07D 213/82 |
| | | | | 564/155 |
| 2017/0367329 | A1 * | 12/2017 | Kobayashi | C07D 213/82 |
| 2020/0262781 | A1 * | 8/2020 | Zaragoza Doerwald | |
| | | | | C07C 209/68 |
| 2020/0281914 | A1 * | 9/2020 | Aoki | A01N 43/40 |

FOREIGN PATENT DOCUMENTS

| | | | | |
|---|---|---|---|---|
| DE | 102022105426 | A1 * | 9/2022 | |
| EP | 2319830 | A1 * | 5/2011 | A01N 37/18 |
| EP | 2835366 | A1 * | 2/2015 | C07C 231/12 |
| FR | 2660923 | A1 * | 10/1991 | |
| IN | 201611011512 | A * | 11/2017 | |
| IN | 202214012005 | A * | 9/2022 | |
| JP | 2011157294 | A * | 8/2011 | |
| JP | 2011157295 | A * | 8/2011 | |
| JP | 2011157296 | A * | 8/2011 | |
| JP | 2012153635 | A * | 8/2012 | |
| WO | 2020169768 | A1 | 8/2020 | |
| WO | WO-2020169768 | A1 * | 8/2020 | B01J 31/2295 |

OTHER PUBLICATIONS

J. Clavel et al., J. Chem. Soc. Perkin Trans. 1 3371-3375 (1992) (Year: 1992).*
S. Jeanmart et al., 24 Bioorganic & Medicinal Chemistry, 317-341 (2016) (Year: 2016).*
C. Luo et al., 24 Organic Process Research & Development, 1024-1031 (2020) (Year: 2020).*
M. Gouda et al., 47 Synthetic Communications, 1269-1300 (2017) (Year: 2017).*
Casreact Abstract J. Clavel et al., FR 2660923 (1991) (Year: 1991).*
First Office Action in IN Patent Application No. 202214012005 dated Sep. 20, 2022.

* cited by examiner

*Primary Examiner* — Alexander R Pagano
(74) *Attorney, Agent, or Firm* — Dilworth IP, LLC

(57) ABSTRACT

The present disclosure provides a preparation method of 4-(heptafluoro-2-propyl)-2-trifluoromethylaniline and an application thereof. The preparation method comprises the following steps: reacting 2-aminobenzotrifluoride and 2-bromoheptafluoropropane in the presence of sodium formate or hydrates thereof and a $SO_2$ reagent, so as to obtain 4-(heptafluoro-2-propyl)-2-trifluoromethylaniline. The present disclosure adds sodium formate or hydrate thereof and the $SO_2$ reagent during the reaction of 2-aminobenzotrifluoride and 2-bromoheptafluoropropane. Under the cooperation of these two compounds, the yield of the reaction is high. And the purity of the product is high, the operation method is simple, the cost is relatively low, and the pH of the reaction doesn't need to be controlled.

10 Claims, No Drawings

PREPARATION METHOD OF 4-(HEPTAFLUORO-2-PROPYL)-2-TRIFLUOROMETHYLANILINE AND APPLICATION THEREOF

TECHNICAL FIELD

The present application relates to the field of organic synthesis, and more particularly to a preparation method of 4-(heptafluoro-2-propyl)-2-trifluoromethylaniline and an application thereof.

BACKGROUND 4-(heptafluoro-2-propyl)-2-trifluoromethylaniline is an important intermediate for the preparation of meta-diamide compound. For example, among the synthesis of pesticide Broflanilide (CAS: 1207727-04-5) and newly covered meta-diamide compound Cyproflanilide (CAS: 2375110-88-4), 4-(heptafluoro-2-propyl)-2-trifluoromethylaniline needs to be used.

European patent EP2319830A1 takes only 30% yield with expensive heptafluoroisopropyl iodide, which is not conducive to industrial production.

Japanese patent JP2012153635A was heptafluoroisopropyl iodide with 2-(trifluoromethyl)aniline in a mixed solvent of water and ethyl acetate, under the catalysis of the phase transfer catalyst, the pH was controlled to 4.9-5.0 by the sodium carbonate solution, and only 85% conversion was obtained. The reaction system is more complicated, and the pH of the reaction needs to be precisely controlled.

The method reported by patent WO2019059412A1 is the same as Japanese Patent JP2012153635A. However, the pH of the reaction in patent WO2019059412A1 needs to be controlled in the range of 4.3-4.5, and the yield is only 81.1%.

Indian patented IN201611011512A, heptafluoroisopropyl iodide replaced with 2-bromoheptafluoropropane, the reaction temperature is 15° C., and other operations are similar to the above-mentioned Japanese patents. The HCl gas was introduced into the crude product to prepare 4-(perfluoropropane-2-yl)-2-trifluoromethyl aniline hydrochloride, and only 83% yield was obtained.

The patented WO2019030187A1 reported, with 2-bromo-heptafluoropropane as alkylating agents, the 4-(heptafluoro-2-propyl)-2-trifluoromethylaniline can be obtained by the catalytic of the acidic substance under a single solvent, but only 78% (based on 2-bromoheptafluoropropane) is obtained, and the raw material is not reacted completely, which causes the purification of the product to be difficult.

Therefore, it is urgent to study a method, with simple operation and high yield and low cost of product, to prepare 4-(heptafluoro-2-propyl)-2-trifluoromethylaniline.

SUMMARY

The present disclosure provides a preparation method of 4-(heptafluoro-2-propyl)-2-trifluoromethylaniline. The products synthesized by this method, with higher yield and higher purity, simple operation and low cost, and the pH does not need to be controlled during the reaction.

In a first aspect, the present disclosure provides a preparation method of 4-(heptafluoro-2-propyl)-2-trifluoromethylaniline, and the preparation methods are as follows:

reacting 2-aminobenzotrifluoride and 2-bromoheptafluoropropane in the presence of sodium formate or hydrates thereof and a $SO_2$ reagent, so as to obtain 4-(heptafluoro-2-propyl)-2-trifluoromethylaniline.

The present disclosure adds sodium formate or hydrates thereof and the $SO_2$ reagent during the reaction of 2-aminobenzotrifluoride and 2-bromoheptafluoropropane. Under the cooperation of these two compounds, the yield of the reaction is high. And the purity of the product is high, the operation method is simple, the cost is relatively low, and the pH of the reaction doesn't need to be controlled.

In the present disclosure, the term "$SO_2$ reagent" refers to the compound to produce $SO_2$, and $SO_2$ is a catalyst in the reaction.

The reaction formula of the present disclosure is as follows:

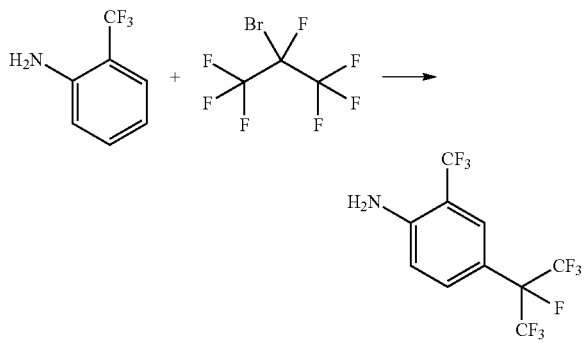

Preferably, a molar ratio of sodium formate or hydrates thereof and 2-aminobenzotrifluoride is (0.1~2):1, such as 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, more preferably (0.6~1.6): 1.

Preferably, a molar ratio of the $SO_2$ reagent and 2-aminobenzotrifluoride is (0.05~2):1, such as 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, more preferably (0.2~1.2):1.

Preferably, a molar ratio of 2-bromoheptafluoropropane and 2-aminobenzotrifluoride is (1.0~2):1, such as 1.1:1, 1.2:1, 1.3:1, 1.4:1, 1.5:1, 1.6:1, 1.7:1, 1.8:1, 1.9:1, more preferably (1.2~1.8):1.

Preferably, the $SO_2$ reagent include any one or at least two combinations of sodium dithionite, $SO_2$, alkali metal sulfite, alkali metal bisulfites, alkaline-earth metal sulfite, alkaline-earth metal bisulfites, $(NH_4)_2SO_3$ or $NH_4HSO_3$, more preferably, any one or at least two combinations of sodium dithionite, $SO_2$, $Na_2SO_3$ or $NaHSO_3$.

Preferably, the reaction system also includes a solvent.

Preferably, the solvent includes any one of or at least two combinations of water, methyl acetate, ethyl acetate, propyl acetate, butyl acetate, isopropyl acetate, tert-butyl acetate, tert-butanol, acetonitrile, propionitrile, 1,4-dioxane, tetrahydrofuran, methyl tert-butyl ether, dichloromethane, 1,2-dichloroethane, trichloromethane, carbon tetrachloride, benzene, toluene or xylenes; more preferably, any one or at least two combinations of water, ethyl acetate, tert-butyl acetate, acetonitrile, propionitrile, tetrahydrofuran, methyl tert-butyl ether, tert-butanol or 1,2-dichloroethane; further more preferably any one or at least two combinations of water, ethyl acetate, acetonitrile, tert-butanol or 1,2-dichloroethane.

Preferably, a mass ratio of the solvent and 2-aminobenzotrifluoride is (1~8):1, such as 1.2:1, 1.4:1, 1.6:1, 1.8:1, 2:1, 2.2:1, 2.4:1, 2.6:1, 2.8:1, 3:1, 3.2:1, 3.4:1, 3.6:1, 3.8:1, 4:1, 4.2:1, 4.4:1, 4.6:1, 4.8:1, 5:1, 5.2:1, 5.4:1, 5.6:1, 5.8:1, 6:1, 6.2:1, 6.4:1, 6.6:1, 6.8:1, 7:1, 7.2:1, 7.4:1, 7.6:1, 7.8:1, more preferably in the range of (4~6):1.

Preferably, the reaction system also includes a phase transfer catalyst.

Preferably, the phase transfer catalyst in this reaction includes tetrabutylammonium hydrogen sulfate.

In the present disclosure, if the solvent of the reaction is a combination of water and insoluble organic solvent, it is necessary to add a phase transfer catalyst. In other cases, there is no need to add a phase transfer catalyst.

Preferably, the reaction temperature is 5° C.~140° C., such as 10° C., 20° C., 30° C., 40° C., 5° C., 60° C., 70° C., 80° C., 90° C., 100° C., 110° C., 120° C., 130° C., more preferably 40° C.~110° C.

Preferably, the reaction time is 2 h~20 h, such as 3 h, 4 h, 5 h, 6 h, 7 h, 8 h, 9 h, 10 h, 11 h, 12 h, 13 h, 14 h, 15 h, 16 h, 17 h, 18 h, 19 h, more preferably 10 h~18 h.

Preferably, the reaction is carried out at a pressure of 0~10 MPa (such as 1 MPa, 2 MPa, 3 MPa, 4 MPa, 5 MPa, 6 MPa, 7 MPa, 8 MPa, 9 MPa), it is preferably conducted at 0.2 MPa~2 MPa.

Preferably, noble gases are introduced into the reaction to improve the pressure of the reaction system.

Preferably, the reaction is carried out in an autoclave.

Preferably, the product of the reaction is required for a post-treatment, and the post-treatment includes the following steps: separating the reaction product to obtain an organic layer, and performing pressure-reduced distillation to the organic layer to remove the solvent, washing, then performing pressure-reduced distillation again to obtain 4-(heptafluoro-2-propyl)-2-trifluoromethylaniline.

Preferably, a method of the separating includes liquid separation or filtration.

Preferably, a detergent of the washing includes sodium carbonate and/or water.

Preferably, the preparation method includes the following steps:

(1) adding 2-aminobenzotrifluoride, a solvent with a mass ratio of (1~8):1 to 2-aminobenzotrifluoride, sodium formate or hydrates thereof with a molar ratio of (0.1~2):1 to 2-aminobenzotrifluoride, a $SO_2$ reagent with a molar ratio of (0.05~2):1 to 2-aminobenzotrifluoride, and 2-bromoheptafluoropropane with a molar ratio of (0.05~2):1 to 2-aminobenzotrifluoride to an autoclave, introducing noble gas into the reaction to obtain a 0~10 MPa system pressure, heating the system to 5° C.~140° C., and reacting for 20 hours to obtain crude products; and (2) separating or filtering the crude product obtained by the step (1) to obtain an organic layer, and performing pressure-reduced distillation to the organic layer to remove the solvent, washing with sodium carbonate and water respectively, and then performing pressure-reduced distillation again to obtain 4-(heptafluoro-2-propyl)-2-trifluoromethylaniline.

In a second aspect, the present disclosure provides 4-(heptafluoro-2-propyl)-2-trifluoromethylaniline prepared by the preparation method described in the first aspect.

Preferably, a purity of 4-(heptafluoro-2-propyl)-2-trifluoromethylaniline is greater than 96%.

In a third aspect, the present disclosure provides a metadiamide compound prepared by using 4-(heptafluoro-2-propyl)-2-trifluoromethylaniline described in the second aspect as an intermediate.

The present disclosure has the following beneficial effects compared to existing technologies.

The present disclosure adds sodium formate or hydrates thereof and the $SO_2$ reagent during the reaction of 2-aminobenzotrifluoride and 2-bromoheptafluoropropane. Under the cooperation of these two compounds, the yield of the reaction is high. The reaction yield is higher than 93%, up to 97%. And the purity of the product is high (>96%), the operation method is simple, the cost is relatively low, and the pH of the reaction doesn't need to be controlled.

DETAILED DESCRIPTION

Representative Examples of the present disclosure will be described in the following Examples. Those skilled in the art should understand that the examples herein are only illustrative, and the present disclosure is not limited thereto. The content (purity) or yield of the Examples and the present disclosure refers to a mass content (purity) or yield, which is not specifically described.

Example 1

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), acetonitrile (164.4 g), sodium formate (63 g, 0.6 mol), sodium hydrosulfite (19.8 g, 0.1 mol) and 2-bromoheptafluoropropane (149.4 g, 0.6 mol) was sequentially added to the 2 L autoclave, nitrogen was introduced to the reaction, and the pressure of the reaction system was 0.2 MPa. The mixture was then stirred at 40° C. for 18 h. After the reaction was completed, the liquid was separated, and acetonitrile was removed from the organic layer under reduced pressure. The residue was washed with 100 g of 10% sodium carbonate solution and 50 g of water to obtain a yellow oil. The crude product was distilled under reduced pressure (3 mmHg, 100° C.) to obtain the target compound (160.9 g). High pressure liquid chromatography external standard method is determined that the purity of the compound is 98.1%, yield 95.9%.

Structural detection: Mass spectrometry: LC/MS[M+1]: m/z=330;

$^1$H NMR (400 MHz, DMSO-$d_6$) ($\delta$[ppm]): $\delta$7.52 (d, J=8.9 Hz, 2H), 7.10 (d, J=8.6 Hz, 1H), 6.38 (s, 2H).

Example 2

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), ethyl acetate (246.6 g), tetrabutylammonium hydrogen sulfate (4.2 g), sodium formate (48.1 g, 0.7 mol), sodium hydrosulfite (69.3 g, 0.35 mol) and 2-bromoheptafluoropropane (199.2 g, 0.8 mol) was sequentially added to the 2 L autoclave, nitrogen was introduced to the reaction, and the pressure of the reaction system was 1.1 MPa. The mixture was then stirred at 60° C. for 14 h. After the reaction was completed, the liquid was separated, and ethyl acetate was removed from the organic layer under reduced pressure. The residue was washed with 100 g of 10% sodium carbonate solution and 50 g of water to obtain a yellow oil. The crude product was distilled under reduced pressure (3 mmHg, 100° C.) to obtain the target compound (162.1 g). High pressure liquid chromatography external standard method is determined that the purity of the compound is 97.9%, yield 96.4%.

Example 3

This example provides a method of preparing 4-(heptafluoro-2-propyl)-2-trifluoromethylaniline, and the specific operation is as follows.

2-aminobenzotrifluoride (82.2 g, 0.5 mol), water (246.6 g), tert-butanol (246.6 g), sodium formate (84 g, 0.8 mol), sodium hydrosulfite (118.8 g, 0.6 mol) and 2-bromoheptafluoropropane (224.1 g, 0.9 mol) was sequentially added to the 2 L autoclave, nitrogen was introduced to the reaction, and the pressure of the reaction system was 2.0 MPa. The mixture was then stirred at 80° C. for 10 h. After the reaction was completed, the liquid was separated, and tert-butanol was removed from the organic layer under reduced pressure. The residue was washed with 100 g of 10% sodium carbonate solution and 50 g of water to obtain a yellow oil. The crude product was distilled under reduced pressure (3 mmHg, 100° C.) to obtain the target compound (164.1 g). High pressure liquid chromatography external standard method is determined that the purity of the compound is 97.5%, yield 97.2%.

Structural detection: Mass spectrometry: LC/MS[M+1]: m/z=330.

Example 4

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), 1,2-dichloroethane (246.6 g), tetrabutylammonium hydrogen sulfate (4.2 g), sodium formate (84 g, 0.8 mol), sodium hydrosulfite (69.3 g, 0.35 mol) and 2-bromoheptafluoropropane (224.1 g, 0.9 mol) was sequentially added to the 2 L autoclave, nitrogen was introduced to the reaction, and the pressure of the reaction system was 1.1 MPa. The mixture was then stirred at 80° C. for 10 h. After the reaction was completed, the liquid was separated, and 1,2-dichloroethane was removed from the organic layer under reduced pressure. The residue was washed with 100 g of 10% sodium carbonate solution and 50 g of water to obtain a yellow oil. The crude product was distilled under reduced pressure (3 mmHg, 100° C.) to obtain the target compound (163.9 g). High pressure liquid chromatography external standard method is determined that the purity of the compound is 97.2%, yield 96.8%.

Structural detection: Mass spectrometry: LC/MS[M+1]: m/z=330.

Example 5

This example provides a method of preparing 4-(heptafluoro-2-propyl)-2-trifluoromethylaniline, and the specific operation is as follows.

2-aminobenzotrifluoride (82.2 g, 0.5 mol), acetonitrile (328.8 g), sodium formate (31.5 g, 0.3 mol), sodium hydrosulfite (19.8 g, 0.1 mol) and 2-bromoheptafluoropropane (149.4 g, 0.6 mol) was sequentially added to the 2 L autoclave, nitrogen was introduced to the reaction, and the pressure of the reaction system was 0.2 MPa. The mixture was then stirred at 70° C. for 18 h. After the reaction was completed, the reaction system was filtered, and acetonitrile was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (160.5 g). High pressure liquid chromatography external standard method is determined that the purity of the compound is 97.1%, yield 94.7%.

Structural detection: Mass spectrometry: LC/MS[M+1]: m/z=330.

Example 6

This example provides a method of preparing 4-(heptafluoro-2-propyl)-2-trifluoromethylaniline, and the specific operation is as follows.

2-aminobenzotrifluoride (82.2 g, 0.5 mol), acetonitrile (411 g), sodium formate (63 g, 0.6 mol), $SO_2$ (12.8 g, 0.2 mol) and 2-bromoheptafluoropropane (174.3 g, 0.7 mol) was sequentially added to the 2 L autoclave, nitrogen was introduced to the reaction, and the pressure of the reaction system was 1.1 MPa. The mixture was then stirred at 90° C. for 16 h. After the reaction was completed, the reaction system was filtered, and acetonitrile was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (158.6 g). High pressure liquid chromatography external standard method is determined that the purity of the compound is 96.9%, yield 93.4%.

Structural detection: Mass spectrometry: LC/MS[M+1]: m/z=330.

Example 7

This example provides a method of preparing 4-(heptafluoro-2-propyl)-2-trifluoromethylaniline, and the specific operation is as follows.

2-aminobenzotrifluoride (82.2 g, 0.5 mol), 1,2-dichloroethane (493.2 g), sodium formate (52.0 g, 0.5 mol), $Na_2SO_3$ (30.9 g, 0.3 mol) and 2-bromoheptafluoropropane (224.1 g, 0.9 mol) was sequentially added to the 2 L autoclave, nitrogen was introduced to the reaction, and the pressure of the reaction system was 2.0 MPa. The mixture was then stirred at 110° C. for 14 h. After the reaction was completed, the reaction system was filtered, and 1,2-dichloroethane was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (159.3 g). High pressure liquid chromatography external standard method is determined that the purity of the compound is 97.0%, yield 93.9%.

Structural detection: Mass spectrometry: LC/MS[M+1]: m/z=330.

Example 8

This example provides a method of preparing 4-(heptafluoro-2-propyl)-2-trifluoromethylaniline, and the specific operation is as follows.

2-aminobenzotrifluoride (82.2 g, 0.5 mol), acetonitrile (328.8 g), sodium formate (52.0 g, 0.5 mol), $NaHSO_3$ (31.2 g, 0.3 mol) and 2-bromoheptafluoropropane (224.1 g, 0.9 mol) was sequentially added to the 2 L autoclave, nitrogen was introduced to the reaction, and the pressure of the reaction system was 1.1 MPa. The mixture was then stirred at 110° C. for 14 h. After the reaction was completed, the reaction system was filtered, and 1,2-dichloroethane was removed from the organic layer under reduced pressure. The residue was washed with 100 g of 10% sodium carbonate solution and 50 g of water to give a yellow oil. The crude product was distilled with reduced pressure (3 mmHg, 100° C.) to obtain the target compound (159.3 g). High pressure liquid chromatography external standard method is determined that the purity of the compound is 97.3%, yield 94.2%.

Structural detection: Mass spectrometry: LC/MS[M+1]: m/z=330.

Example 9

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), acetonitrile (164.4 g), sodium formate (5.25 g, 0.05 mol), sodium hydrosulfite (19.8 g, 0.1 mol) and 2-bromoheptafluoropropane (149.4 g, 0.6 mol) was sequentially added to the 2 L autoclave, nitrogen was introduced to the reaction, and the pressure of the reaction system was 0.2 MPa. The mixture was then stirred at 40° C. for 18 h. After the reaction was completed, the liquid was separated, and acetonitrile was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (125.9 g). High pressure liquid chromatography external standard method is determined that the purity of the compound is 99.1%, yield 75.8%.

Structural detection: Mass spectrometry: LC/MS[M+1]: m/z=330.

Example 10

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), ethyl acetate (164.4 g), sodium formate (15.75 g, 0.15 mol), sodium hydrosulfite (19.8 g, 0.1 mol) and 2-bromoheptafluoropropane (149.4 g, 0.6 mol) was sequentially added to the 2 L autoclave, nitrogen was introduced to the reaction, and the pressure of the reaction system was 0.2 MPa. The mixture was then stirred at 40° C. for 14 h. After the reaction was completed, the liquid was separated, and ethyl acetate was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (132.7 g). High pressure liquid chromatography external standard method is determined that the purity of the compound is 99.2%, yield 80.0%.

Structural detection: Mass spectrometry: LC/MS[M+1]: m/z=330.

Example 11

This example provides a method of preparing 4-(heptafluoro-2-propyl)-2-trifluoromethylaniline, and the specific operation is as follows.

2-aminobenzotrifluoride (82.2 g, 0.5 mol), water (164.4 g), tert-butanol (164.4 g), sodium formate (26.25 g, 0.25 mol), sodium hydrosulfite (19.8 g, 0.1 mol) and 2-bromoheptafluoropropane (149.4 g, 0.6 mol) was sequentially added to the 2 L autoclave, nitrogen was introduced to the reaction, and the pressure of the reaction system was 0.2 MPa. The mixture was then stirred at 40° C. for 10 h. After the reaction was completed, the liquid was separated, and tert-butanol was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (142.1 g). High pressure liquid chromatography external standard method is determined that the purity of the compound is 99.1%, yield 85.6%.

Structural detection: Mass spectrometry: LC/MS[M+1]: m/z=330.

Example 12

This example provides a method of preparing 4-(heptafluoro-2-propyl)-2-trifluoromethylaniline, and the specific operation is as follows.

2-aminobenzotrifluoride (82.2 g, 0.5 mol), acetonitrile (328.8 g), sodium formate (104.0 g, 1.0 mol), $NaHSO_3$ (31.2 g, 0.3 mol) and 2-bromoheptafluoropropane (224.1 g, 0.9 mol) was sequentially added to the 2 L autoclave, nitrogen was introduced to the reaction, and the pressure of the reaction system was 1.1 MPa. The mixture was then stirred at 110° C. for 10 h. After the reaction was completed, the liquid was separated, and tert-butanol was removed from the organic layer under reduced pressure. The residue was washed with 100 g of 10% sodium carbonate solution and 50 g of water to obtain a yellow oil. The crude product was distilled with reduced pressure (3 mmHg, 100° C.) to obtain the target compound (156.2 g). High pressure liquid chromatography external standard method is determined that the purity of the compound is 97.0%, yield 92.1%.

Structural detection: Mass spectrometry: LC/MS[M+1]: m/z=330.

Comparative Example 1

The difference from Example 1 is that sodium formate is replaced with the same amount of substance sodium carbonate. Liquid separation after reaction, high pressure liquid chromatography external standard method is determined that the yield of the target compound is 61.3%.

Structural detection: Mass spectrometry: LC/MS[M+1]: m/z=330.

The above results demonstrate that the preparation method provided by the present disclosure has a high yield. The yield is higher than 93%, up to 97%.

Comparative example 1 only replaced sodium dihydrate with sodium carbonate, and the yield of the reaction is significantly reduced. This proves that the addition of sodium dihydrate in the present disclosure plays a crucial effect on the increase of yields.

The present disclosure illustrates the detailed method of the present disclosure by the above examples. However, the present disclosure is not limited to the above detailed method. It does not mean that the present disclosure must rely on the above detailed method to implement. Those skilled in the art should understand that any improvements of the disclosure (equivalent replacement of all raw materials of the products of the present disclosure, addition of auxiliary components, or the selection of specific methods, etc.) are within the scope of the disclosure.

What is claimed is:

1. A preparation method of 4-(heptafluoro-2-propyl)-2-trifluoromethylaniline, comprising:
reacting 2-aminobenzotrifluoride and 2-bromoheptafluoropropane in the presence of sodium formate or hydrates thereof and a $SO_2$ reagent, so as to obtain 4-(heptafluoro-2-propyl)-2-trifluoromethylaniline.

2. The preparation method according to claim 1, wherein a molar ratio of sodium formate or hydrates thereof and 2-aminobenzotrifluoride is (0.1~2):1.

3. The preparation method according to claim 1, wherein a molar ratio of the $SO_2$ reagent and 2-aminobenzotrifluoride is (0.05~2)1.

4. The preparation method according to claim 1, wherein a molar ratio of 2-bromoheptafluoropropane and 2-aminobenzotrifluoride is (1.0~2):1.

5. The preparation method according to claim 1, wherein the $SO_2$ reagent include any one or at least two combinations of sodium dithionite, $SO_2$, alkali metal sulfite, alkali metal bisulfites, alkaline-earth metal sulfite, alkaline-earth metal bisulfites, $(NH_4)_2SO_3$ or $NH_4HSO_3$.

6. The preparation method according to claim 1, wherein the reaction system also includes a solvent, wherein the solvent includes any one of or at least two combinations of water, methyl acetate, ethyl acetate, propyl acetate, butyl acetate, isopropyl acetate, tert-butyl acetate, tert-butanol, acetonitrile, propionitrile, 1,4-dioxane, tetrahydrofuran, methyl tert-butyl ether, dichloromethane, 1,2-dichloroethane, trichloromethane, carbon tetrachloride, benzene, toluene or xylenes.

7. The preparation method according to claim 1, wherein the reaction system also includes a phase transfer catalyst, wherein the phase transfer catalyst includes tetrabutylammonium hydrogen sulfate.

8. The preparation method according to claim 1, wherein the reaction temperature is 5° C~140° C., the reaction time is 2 h~20 h, and the reaction is carried out at a pressure of 0~10 MPa.

9. The preparation method according to claim 1, wherein noble gases are introduced into the reaction to improve the pressure of the reaction system.

10. The preparation method according to claim 1, wherein the preparation method comprises the following steps:
(1) adding 2-aminobenzotrifluoride, a solvent with a mass ratio of (1~8):1 to 2-aminobenzotrifluoride, sodium formate or hydrates thereof with a molar ratio of (0.1~2):1 to 2-aminobenzotrifluoride, a $SO_2$ reagent with a molar ratio of (0.05~2):1 to 2-aminobenzotrifluoride, and 2-bromoheptafluoropropane with a molar ratio of (0.05~2)1 to 2-aminobenzotrifluoride to an autoclave, introducing noble gas into the reaction to obtain a 0~10 MPa system pressure, heating the system to 5° C~140° C., and reacting for 20 hours to obtain crude products; and
(2) separating or filtering the crude product obtained by the step (1) to obtain an organic layer, and performing pressure-reduced distillation to the organic layer to remove the solvent, washing with sodium carbonate and water respectively, and then performing pressure-reduced distillation again to obtain 4-(heptafluoro-2-propyl)-2-trifluoromethylaniline.

* * * * *